United States Patent
Xiao et al.

(10) Patent No.: US 6,803,493 B1
(45) Date of Patent: Oct. 12, 2004

(54) TOLUENE DISPROPORTION PROCESS

(75) Inventors: Xin Xiao, Houston, TX (US); Becky Fussell, Pasadena, TX (US)

(73) Assignee: Fina Technology, Inc., Houston, TX (US)

( * ) Notice: Subject to any disclaimer, the term of this patent is extended or adjusted under 35 U.S.C. 154(b) by 0 days.

(21) Appl. No.: 10/642,030

(22) Filed: Aug. 15, 2003

(51) Int. Cl.[7] .......................... C07C 5/52; C10G 47/04
(52) U.S. Cl. ................... 585/475; 585/470; 208/135; 208/111.01
(58) Field of Search .............................. 585/475, 470; 208/135, 111.01

(56) References Cited

U.S. PATENT DOCUMENTS

| | | |
|---|---|---|
| 3,436,174 A | 4/1969 | Sand |
| 3,476,821 A | 11/1969 | Brandenburg et al. |
| 3,480,539 A | 11/1969 | Voorhies, Jr. et al. |
| 3,780,122 A | 12/1973 | Pollitzer |
| 3,928,174 A * | 12/1975 | Bonacci et al. .............. 208/80 |
| 4,723,049 A | 2/1988 | Menard et al. |

* cited by examiner

Primary Examiner—Thuan Dinh Dang
(74) Attorney, Agent, or Firm—William D. Jackson

(57) ABSTRACT

A process for the disproportionation of toluene over a mordenite catalyst with a feedstock of a lower than normal toluene content and having a significant content of non-aromatic hydrocarbons, having from 6–8 carbon atoms. A toluene feedstock and a hydrogen co-feed are supplied to reaction zone containing a mordenite disproportionation catalyst. The feedstock has a toluene content of 80–90 wt. % and a $C_6$–$C_8$ non-aromatic content of 10–20 wt. %. The reaction zone is at temperature and pressure effective to cause a disproportionation of the toluene to benzene and xylene with the concomitant cracking of the non-aromatic hydrocarbons to lower molecular weight hydrocarbons. A product stream comprising toluene, benzene, xylene and $C_2$–$C_4$ aliphatic hydrocarbons is recovered from the reaction zone. The mordenite catalyst is promoted with a metal such as nickel, palladium or platinum to enhance the hydrogenation activity of the catalyst.

19 Claims, 1 Drawing Sheet

TOLUENE DISPROPORTION PROCESS

FIELD OF THE INVENTION

This invention relates to the disproportionation of alkylaromatic feedstreams and more particularly to the disproportionation of toluene containing feedstocks employing mordenite catalysts of low aluminum content.

BACKGROUND OF THE INVENTION

The disproportionation of toluene involves a well known transalkylation reaction in which toluene is converted to benzene and xylene in accordance with the following reaction which is mildly exothermic.

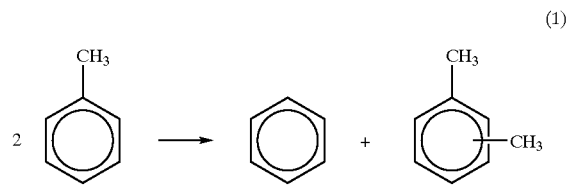

(1)

Mordenite is one of a number of catalysts commonly employed in the transalkylation of alkylaromatic compounds. Mordenite is a crystalline aluminosilicate zeolite having a network of silicon and aluminum atoms interlinked in its crystalline structure through oxygen atoms. For a general description of mordenite catalysts, reference is made to Kirk-Othmer Encyclopedia of Chemical Technology, 3rd Edition, 1981,under the heading "Molecular Sieves", Vol. 15, pages 638–643. Mordenite, as found in nature or as synthesized, typically has a relatively low silica to alumina mole ratio of about 10 or less. Such conventionally structured mordenite catalysts are commonly employed in the disproportionation of toluene. However, mordenite catalysts having substantially lower alumina content are also employed in the disproportionation of toluene.

The aluminum deficient mordenite catalysts have a silica/alumina ratio greater than 10 and may sometimes range up to about 100. Such low alumina mordenites may be prepared by direct synthesis as disclosed, for example, in U.S. Pat. No. 3,436,174 to Sand or by acid extraction of a more conventionally prepared mordenite as disclosed in U.S. Pat. No. 3,480,539 to Voorhies et al. U.S. Pat. No. 3,780,122 to Pollitzer discloses the transalkylation of toluene using a mordenite zeolite having a silica/alumina ratio greater than 10 which is obtained by acid extraction of a mordenite zeolite having a silica/alumina ratio of less than 10.

The disproportionation of toluene feedstocks may be carried out at temperatures ranging from about 200° C. to about 600° C. or above and at pressures ranging from atmospheric to perhaps 100 atmospheres or above. However, the catalyst itself may impose constraints on the reaction temperatures in terms of catalyst activity and aging characteristics. In general, the prior art indicates that while relatively high temperatures can be employed for the high aluminum mordenites (low silica to alumina ratios) somewhat lower temperatures should be employed for the low alumina mordenites. Thus, where mordenite catalysts having high silica/alumina ratios have been employed in the transalkylation of alkylaromatics, it has been the practice to operate toward the lower end of the temperature range. It is also a common practice in this case to promote the catalyst with a catalytically active metallic content, as disclosed, for example, in U.S. Pat. No. 3,476,821 to Brandenburg. Metal promoters are said to substantially increase activity and catalyt life.

It is conventional practice to supply hydrogen along with toluene to the reaction zone. While the disproportionation reaction (1) is net of hydrogen, the use of a hydrogen co-feed is generally considered to prolong the useful life of the catalyst, as disclosed, for example, in the above patent to Brandenburg. The amount of hydrogen supplied, which can be measured in terms of the hydrogen/toluene mole ratio or in terms of a standard liter of hydrogen per liter of feedstock, is generally shown in the prior art to increase as temperature increases. Normally, the hydrocarbon feedstock supplied to the toluene disproportionation reaction zone is of extremely high purity. Typically, feedstocks having a toluene content of 90–99 wt. % are supplied to the reaction zone. Usually it is considered desirable to maintain the toluene content in excess of 99 wt. % (less than 1% impurities) in order to avoid unacceptably rapid catalyst deactivation. Thus the atmosphere within the reaction zone is, in addition to the hydrogen co-feed, toluene reactant and benzene and xylene products.

SUMMARY OF THE INVENTION

In accordance with the present invention there is provided a novel process for the disproportionation of toluene over a mordenite catalyst under conditions in which the feedstock has a lower toluene content than normally encountered and contains, in addition, a significant content of non-aromatic hydrocarbons, typically containing from 6–8 carbon atoms. In carrying out the invention, a toluene feedstock and a hydrogen co-feed are supplied to a reaction zone containing a mordenite-type disproportionation catalyst. The toluene feedstock has a toluene content within the range of 80–90 wt. % toluene and a $C_6$–$C_8$ non-aromatic content within the range of 10–20 wt. %. The reaction zone is operated under temperature and pressure conditions effective to cause a disproportionation of the toluene to benzene and xylene with the concomitant cracking of the non-aromatic hydrocarbons to convert a predominant portion of the non-aromatic hydrocarbon content to lower molecular weight hydrocarbons and produce a lower boiling fraction in the LPG boiling range. A product stream comprising toluene, benzene, xylene and $C_2$–$C_4$ aliphatic hydrocarbons is recovered from the reaction zone.

In a preferred embodiment of the invention, the mordenite catalyst is promoted with a metal which is effective to enhance the hydrogenation activity of the catalyst. In one application of the invention, the mordenite catalyst is promoted with nickel. In another, the mordenite catalyst is promoted with palladium or platinum. Preferred operating conditions for the invention involve a reaction zone temperature within the range of 300°–500° C. and an average pressure within the reaction zone within the range of 20–60 bars. The feedstock is supplied to the reaction zone to provide a liquid hourly space velocity (LHSV) within the range of 0.5 hours$^{-1}$–4.0 hours$^{-1}$.

In a further aspect of the invention, there is provided a toluene disproportion process in which the reaction severity conditions in the reaction zone are adjusted in order to accommodate the toluene content of the feedstock. In carrying out this aspect of the invention, there is supplied to the reaction zone a first toluene continuing feedstock having a first relatively high toluene content. Hydrogen is also supplied to the reaction zone. The reaction zone is operated under reaction severity conditions of space velocity, temperature and pressure effective to cause disproportionation of the toluene in the feedstock to benzene and xylene and a product stream containing toluene, benzene and xylene as recovered from the reaction zone. Thereafter, a second toluene-containing feedstock is supplied to the reaction zone. The second toluene-containing feedstock has a second toluene content, which is lower than the toluene content of the first highly pure feedstock, and also has a $C_6$–$C_8$ non-aromatic content which is greater than any content of $C_6$–$C_8$ non-aromatic hydrocarbons in the first feedstock. Concomitantly with the supply of the second feedstock, the reaction zone is operated under reaction severity conditions of space velocity, temperature, and pressure which are more severe than the reaction severity conditions of the reaction zone when supplied with the highly pure toluene feedstock. The more severe reaction conditions are effective to cause disproportionation of the toluene to benzene and xylene with concomitant cracking of the non-aromatic hydrocarbons to convert the predominant portion of the non-aromatic hydrocarbon content to lower molecular weight hydrocarbons to produce a lower boiling fraction in the LPG boiling range. The product stream recovered from the reaction zone contains toluene, benzene, xylene and $C_2$–$C_4$ hydrocarbons. Preferably in this aspect of the invention, the reaction zone under the more severity reaction conditions involves a lower space velocity and preferably also a higher pressure than operation of the reaction zone during feed of the highly pure toluene feedstock.

Preferably the second feedstock has a toluene content which is lower than the toluene content of the first feedstock by an incremental amount of at least an 8 wt. %. Further, the second feedstock contains $C_6$–$C_8$ non-aromatic hydrocarbons in an amount which is incrementally at least 8 wt. % greater than the content of any $C_6$–$C_8$ non-aromatic hydrocarbons in the first feedstream. In a specific application of the invention the toluene content of the first feedstock has a toluene purity greater than 90 wt. % and the toluene content of the second feedstock is within the range of 80–90 wt. % toluene and has a $C_6$–$C_8$ non-aromatic content he range of 10–20 wt. %.

DETAILED DESCRIPTION OF THE INVENTION

Figure 1:
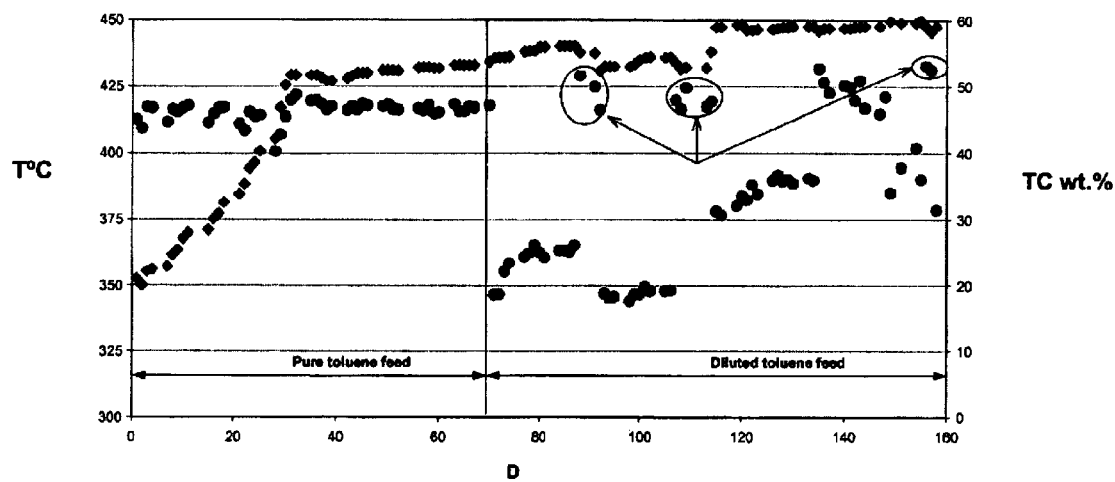
FIG. 1 is a graph illustrating temperature and toluene conversion as a function of time and toluene content of the feedstock to a reaction zone containing a nickel mordenite catalyst.

As noted previously, the conventional wisdom in toluene disproportionation processes is that the toluene feedstock should be essentially pure toluene with little or no content of non-aromatic hydrocarbons such as alkanes, olefins and cycloalkanes. The present invention offers a departure from the conventional wisdom by operating a toluene disproportion reaction zone under reaction severity conditions effective to carry out the disproportionation reaction under conditions of higher severity which result in toluene conversion while at the same time converting the non-aromatic content of the feedstock to lower molecular weight hydrocarbons.

In experimental work with respect to the invention, two toluene feedstocks were employed in a toluene disproportionation reactor. One feedstock employed a highly pure toluene having an at least 99 wt. % toluene with only very minor amounts of non-aromatics, such as $C_6$–$C_8$ alkanes and also very minor amounts of $C_6$–$C_8$ aromatics such as benzene, ethylbenzene or xylene. The other toluene-containing feedstock was a diluted toluene containing about 82 wt. % toluene and about 18 wt. % non-aromatics. The overall composition of the diluted and pure toluene stream is set forth in Table 1,and the composition of the non-aromatic content of the diluted toluene stream is set forth in Table 2.

TABLE 1

|  | Diluted Toluene | Pure Toluene |
| --- | --- | --- |
| Total nonaromatics | 18.239 | 0.040 |
| Benzene | 0.081 | 0.014 |
| Toluene | 81.662 | 99.915 |
| Ethylbenzene | 0.010 | 0.011 |
| m-Xylene | 0.003 | 0.006 |
| p-Xylene | 0.005 | 0.005 |
| Other | 0.000 | 0.009 |
| Total | 100.000 | 100.000 |

TABLE 2

| | |
| --- | --- |
| Dimethyl pentane | 0.104 |
| Methyl hexane | 2.279 |
| Dimethyl pentane | 0.965 |
| Dimethyl cyclopentane | 0.027 |
| Methyl hexane | 4.735 |
| Heptene | 0.041 |
| Dimethyl cyclopentane | 0.146 |
| Dimethyl cyclopentane | 0.150 |
| Ethyl pentane | 0.941 |
| Dimethyl cyclopentane | 0.250 |
| Cyclopropyl butane | 0.113 |
| Methyl hexene | 0.100 |
| 3-Heptene | 0.109 |
| n-Heptane | 5.084 |
| Heptene | 0.109 |
| Heptene | 0.082 |
| Heptene | 0.209 |
| Heptene | 0.173 |
| Cyclohexane, methyl- | 0.318 |
| Dimethyl Hexane | 0.155 |
| Cyclopentane, ethyl- | 0.073 |
| Hexane, 2,5-dimethyl- | 0.109 |
| Hexane, 2,4-dimethyl- | 0.209 |
| Hexane, 3,3-dimethyl- | 0.100 |
| Hexane, 2,3-dimethyl- | 0.141 |
| Unknown | 0.046 |
| Heptane, 2-methyl- | 0.369 |
| Heptane, 4-methyl- | 0.173 |
| Hexane, 3,4-dimethyl- | 0.059 |
| Heptane, 3-methyl- | 0.382 |
| Hexane, 3-ethyl- | 0.119 |
| Cyclohexane, 1,2-dimethyl-, trans- | 0.027 |
| n-Octane | 0.341 |
| Total | 18.239 |

The toluene disproportionation runs were carried out in a downflow reactor containing a nickel mordenite disproportionation catalyst formulated of about 70% mordenite and about 30% alumina support The catalyst was promoted with about 1% nickel. As discussed in greater detail below, the toluene feedstocks were supplied to the reactor to provide liquid hourly space velocities (LHSV) of about 1.3–3.0 hrs.$^{-1}$ The ratio of hydrogen to total hydrocarbon content of toluene or toluene plus the impurities varied from about 650–3,000 standard liters of hydrogen per liter of hydrocarbon feed. The temperature ranged from about 430° C.–450° C. and the reactor inlet pressure varied from 41–55 bars. The catalyst was employed in an amount of 30 ml, and was in the form of 14–20 mesh mordenite particles.

Figure 2:
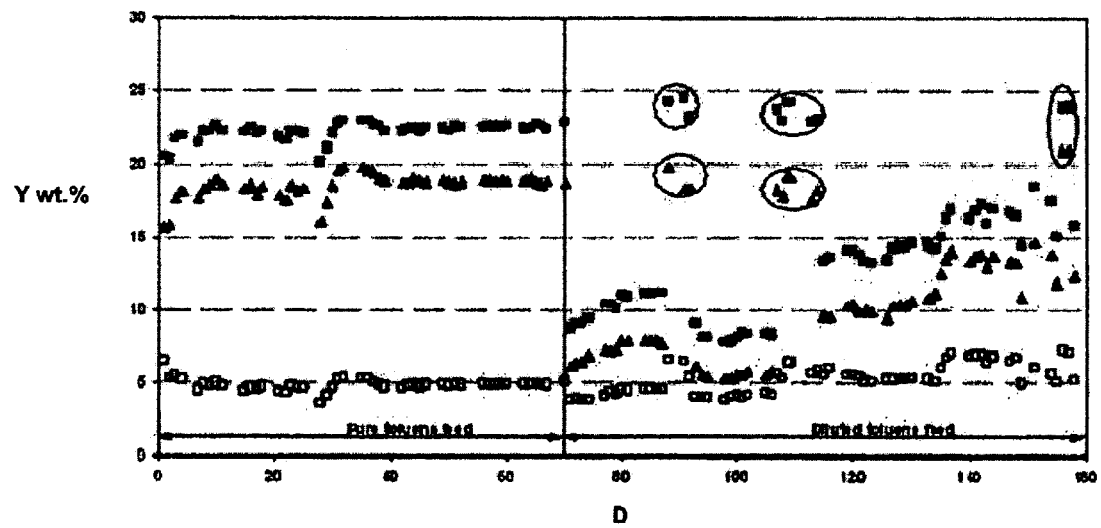
FIG. 2 is a graph illustrating the selectivity in terms of xylene, benzene and heavies yields as a function of time and toluene content of the feedstock.

In the experimental work, the initial feed of pure toluene (99+wt % toluene) was introduced into the reactor for an initial 70-day period. Thereafter, the feed was switched to the dilute toluene feedstock and continued for an additional 90 days with interruption intervals at day 90 and day 100, during which intervals, the pure toluene feed was reinstituted. The operating conditions and selectivity values during the course of the 160 day run are illustrated in FIGS. 1 and 2. In FIG. 1, toluene conversion, TC, in wt % (●) and temperature, T, in ° C. (♦) are plotted on the ordinate versus the Days-On-Stream, D, on the abscissa. In FIG. 2, the xylenes yield (■), benzene yield (▲) and heavies yield (□), Y, all in weight percent of the product, are plotted on the ordinate versus the time in stream, D, in days on the abscissa. In both FIGS. 1 and 2, the excursions from diluted toluene feed to pure toluene are circled at days 90, 110 and at the conclusion of the run. The product distribution from the diluted toluene stream at various temperatures, pressures, hydrogen/hydrocarbon ratios and space velocity are tabulated in Table 3.

As can be seen from an examination of FIGS. 1 and 2, the run with the pure toluene stabilized in terms of temperature and toluene conversion at about day 30, and then increased with a modest deactivation rate of about 0.14° F. per day until day 70 when the feedstream was switched from the pure toluene to the diluted toluene. Toluene conversion dropped immediately from about 47% to about 18.7% when the overall reaction severity was maintained the same as with the pure toluene feed. This 18.7% toluene conversion was equivalent to about 47% for pure toluene as evidenced by the data shown at days 90 and 110, when the feed was switched from the diluted toluene back to the pure toluene. The catalyst deactivation rate during the diluted toluene injection was about the same as the rate of 0.14° F./day observed for the pure toluene feed. As indicated by the data in FIG. 2, the benzene, xylenes and heavies yields during the dilute stock toluene feed were about 5.8%, 8.5% and 4%, respectively. These values corresponded to normal toluene disproportionation yields with the pure toluene stream of 18%, 22% and 5.2% of benzenes, xylenes and heavies. The low yields resulted from the low conversion of the diluted toluene, whereas the relatively higher heavies content was caused by alkylation of cracked nonaromatics. The heavies in the reaction mixture also shifted the equilibrium from benzene to xylenes. Cracking of non-aromatics was evidenced by the decrease in methylcyclopentane from about 4.24 wt. % in the feed to about 3.08 wt. % in the reactor effluent. Total non-aromatics content decreased from about 18.28% to about 16.1 wt. % of which over half were gases. The liquid yield was 90.65% (99.3 wt. % from toluene disproportionation) and the ethylbenzene/$C_8$ aromatic ratio was at 3.07 (1.6% from toluene disproportionation). The off gases were about 38% propane, 19% isobutene, 18% ethane and 12% propylene.

During an initial period of 77–87 days, the run conditions were set at a higher severity corresponding to the conversion of 51.2 wt. % pure toluene. Here the conversion of toluene in the diluted stream was 26.6 wt. %. The liquid yield decreased to 86.6% attendant to the production of more gases. The yields of benzenes, xylenes and heavies were about 7.9 wt. %, 11.1 wt. % and 4.5 wt. %, respectively.

In order to increase toluene conversion, the process conditions were changed by increasing the pressure from 41 to 55 bars, increasing the hydrogen to oil ratio from 3:1 to 6:1 (an increase from 650 to 1,300 standard liters per liter), and decreasing the LHSV from 2.9 to 1.3. The average results achieved by varying the processing conditions of temperature, pressure, hydrogen to oil ratio and space velocity are summarized in Table 3.

TABLE 3

| | | | | | | | |
|---|---|---|---|---|---|---|---|
| Temp, ° C. | 433 | 440 | 447 | 448 | 447 | 449 | 449 |
| Pressure, barg | 41 | 41 | 55 | 55 | 55 | 55 | 41 |
| $H_2$ to oil, std liter/liter | 648 | 652 | 668 | 1304 | 2915 | 1934 | 1789 |
| LHSV, $hr^{-1}$ | 2.9 | 2.9 | 2.8 | 2.9 | 1.3 | 2.0 | 2.1 |
| Toluene Conv., wt % | 20.1 | 26.6 | 33.4 | 37.0 | 50.7 | 46.5 | 35.9 |
| $H_2$ consumption, std l/l | 71 | 82 | 101 | 201 | 497 | 388 | 337 |
| Product Distrib., wt % | | | | | | | |
| Total | | | | | | | |
| Nonaromatics | 16.08 | 16.43 | 15.77 | 17.67 | 22.18 | 17.94 | 14.78 |
| Ethylbenzene | 0.27 | 0.43 | 0.64 | 0.73 | 1.10 | 1.10 | 0.79 |
| Benzene | 5.82 | 7.81 | 9.96 | 10.53 | 13.53 | 13.65 | 11.97 |
| Toluene | 65.41 | 59.93 | 54.64 | 51.68 | 40.10 | 43.67 | 52.18 |
| Xylenes | 8.42 | 10.94 | 13.60 | 14.22 | 16.31 | 16.92 | 15.27 |
| $C_9$ | 1.58 | 2.23 | 2.94 | 3.01 | 4.47 | 4.14 | 3.13 |
| $C_{10}$ | 1.14 | 0.80 | 0.79 | 0.61 | 0.52 | 0.75 | 0.47 |
| $C_{11+}$ | 1.28 | 1.43 | 1.66 | 1.53 | 1.78 | 1.84 | 1.42 |
| Liquid yield, wt % | 90.65 | 86.56 | 86.78 | 84.31 | 78.19 | 82.78 | 86.93 |
| Liquid distribution, wt % | | | | | | | |
| Nonarom in liquid | 7.43 | 3.46 | 2.94 | 2.35 | 0.47 | 0.87 | 1.96 |
| Ethylbenzene | 0.29 | 0.50 | 0.74 | 0.87 | 1.41 | 1.33 | 0.90 |
| Benzene | 6.42 | 9.02 | 11.48 | 12.49 | 17.31 | 16.49 | 13.77 |
| Toluene | 72.15 | 69.23 | 62.96 | 61.30 | 51.28 | 52.75 | 60.02 |
| Xylenes | 9.29 | 12.64 | 15.67 | 16.87 | 20.86 | 20.43 | 17.56 |
| C9 | 1.75 | 2.58 | 3.39 | 3.58 | 5.72 | 5.00 | 3.60 |
| C10 | 1.26 | 0.92 | 0.91 | 0.72 | 0.66 | 0.90 | 0.54 |
| $C_{11+}$ | 1.41 | 1.65 | 1.92 | 1.82 | 2.28 | 2.22 | 1.64 |

After increasing the pressure from 41 to 51 bars (equivalent to a 53 wt.% conversion of pure toluene), the toluene conversion for the diluted stream increased to 33.4%. The conversion was further increased to 37% by doubling the hydrogen to oil ratio from about 650 to 1,300 normal liters of hydrogen per liter of liquid feed. The total non-aromatics increased to 22.18%, indicating some ring loss. At the same condition but at a space velocity of 2.0 LHSV, the conversion decreased to 46.5% with the yield of benzene, $C_8$, and heavies remaining constant at 13.65, 16.92 and 6.73 wt.%, respectively. The liquid yields were 78.2% at 50.7 toluene conversion and 82.8 wt% at 46.5 wt. % toluene conversion. The process conditions for the 46.5 conversion of the diluted toluene stream were pressure of 55 bars, space velocity of 2.0 LHSV and hydrogen feed ratio of 1,900 standard liters per liter. The hydrogen consumption was 388 standard liters per liter. When the pressure was decreased to 41 bars, the toluene conversion, as indicated in Table III, decreased to 34.9%, illustrating a clear influence of the reactor pressure to toluene conversion.

As indicated previously, the foregoing experimental work was carried out using a nickel-promoted mordenite catalyst. The presence of nickel in the catalyst enhances the hydrogenation activity of the catalyst. In addition, the catalyst activity is enhanced by increasing the temperature, reactor pressure, the hydrogen to oil ratio, and by decreasing the space velocity. As indicated above, by an appropriate adjustment of these factors, a feedstock having a diluted toluene content can be employed to effectively disproportionate the toluene to benzene and xylene accompanied by cracking of the substantial non-aromatic content of the feedstock to produce lower molecular weight hydrocarbons.

The use of the nickel with the mordenite catalyst to enhance the hydrogenation function of the catalyst thus works with the higher severity reaction conditions to promote the disproportionation and cracking functions observed for the feedstock having a relatively low toluene content and a relatively high non-aromatic content. This can be further enhanced through the use of noble metals, specifically platinum and palladium which function to increase the hydrogenation activity of the mordenite catalyst. The metal promoter for the catalyst normally should be present in an amount of about 0.01–5.0 wt. % of the mordenite. As indicated by the experimental work, 1% nickel is effective. Somewhat lower amounts of e.g. about 0.02–0.05 wt. % of palladium and platinum can be employed where these noble metals are substituted for nickel.

The mordenite catalyst employed in the present invention typically will take the form of an aluminum deficient mordenite as described above. The silica-alumina ratio of such mordenites preferably will be within the range of about 20 to 50. While lower alumina mordenite contents can be employed in carrying out the invention, it usually will be desirable to provide for a silica-alumina ratio of at least 10 and, preferably, at least 20.

Having described specific embodiments of the present invention, it will be understood that modification thereof may be suggested to those skilled in the art, and it is intended to cover all such modifications as fall within the scope of the appended claims.

What is claimed is:

1. A process for the disproportionation of a toluene containing feedstock comprising:
   (a) providing a reaction zone containing a mordenite-type toluene disproportionation catalyst;
   (b) supplying a toluene feedstock having a toluene content within the range of 80–90 wt. % toluene and a $C_6$–$C_8$ non-aromatic content within the range of 10–20 wt. % to said reaction zone;
   (c) supplying hydrogen to said reaction zone;
   (d) operating said reaction zone under temperature and pressure conditions effective to cause the disproportionation of said toluene to benzene and xylene and concomitantly cracking of said non-aromatic hydrocarbons to convert the predominant portion of said non-aromatic hydrocarbon content to lower molecular weight hydrocarbons to produce a lower boiling fraction in the LPG boiling range; and
   (e) recovering a product stream from said reaction zone containing toluene, benzene and xylene, together with $C_2$–$C_4$ hydrocarbons.

2. The process of claim 1 wherein said catalyst is promoted with a metal effective to enhance the hydrogenation activity of the catalyst.

3. The method of claim 2 wherein said mordenite disproportionation catalyst is promoted with nickel.

4. The method of claim 2 wherein said mordenite disproportionation catalyst is promoted with platinum or palladium.

5. The method of claim 1 wherein feedstock is supplied to said reaction zone to provide a liquid hourly space velocity within the range of 0.5 hrs.$^{-1}$–4.0 hrs.$^{-1}$ and said reaction zone is operated at a temperature within a range of 300–500° C. and an average pressure within the range of 20–60 bar.

6. A process for the disproportionation of a toluene containing feedstock comprising:
   (a) providing a reaction zone containing a mordenite-type toluene disproportionation catalyst;
   (b) supplying a first toluene containing feedstock having a first toluene content to said reaction zone;
   (c) supplying hydrogen to said reaction zone;
   (d) operating said reaction zone under reaction severity conditions of space velocity temperature and pressure effective to cause the disproportionation of the toluene in the feedstock to benzene and xylene;
   (e) recovering a product stream from said reaction zone containing toluene, benzene and xylene;
   (f) thereafter supplying a second toluene containing feedstock having a second toluene content which is lower than said first toluene content and also having a $C_6$–$C_8$ nonaromatic content which is greater than the content of any $C_6$–$C_8$ nonaromatic hydrocarbons in said first feedstock to said reaction zone;
   (g) operating said reaction zone under reaction severity conditions of space velocity temperature and pressure which are more severe than the reaction severity conditions of subparagraph (d), and which are effective to cause the disproportionation of said toluene to benzene and xylene with concomitant cracking of said nonaromatic hydrocarbons to convert the predominant portion of nonaromatic hydrocarbon content to lower molecular weight hydrocarbons to produce a lower boiling fraction in the LPG boiling range; and
   (h) recovering a product stream from said reaction zone containing toluene, benzene and xylene, together with $C_2$–$C_4$ hydrocarbons.

7. The process of claim 6 wherein said reaction zone is operated in subparagraph (g) at a lower space velocity than the reaction zone in subparagraph (d).

8. The process of claim 6 wherein said reaction zone is operated in subparagraph (g) at a pressure which is greater than the pressure of said reaction zone in the operation of subparagraph (d).

9. The process of claim 6 wherein said second feedstock has a second toluene content which is lower than the toluene content of said first feedstock by an incremental amount of at least 8 wt. %.

10. The process of claim 9 wherein said second feedstock contains $C_6$–$C_8$ non-aromatic hydrocarbons in an incremental amount which is at least 8 wt. % greater than the content of any $C_6$–$C_8$ non-aromatic hydrocarbons in said first feedstream.

11. The process of claim 6 wherein said catalyst is promoted with a metal effective to enhance the hydrogenation activity of the catalyst.

12. The method of claim 11 wherein said mordenite disproportionation catalyst is promoted with nickel.

13. The method of claim 11 wherein said mordenite disproportionation catalyst is promoted with platinum or palladium.

14. A process for the disproportionation of a toluene containing feedstock comprising:
   (a) providing a reaction zone containing a mordenite-type toluene disproportionation catalyst;
   (b) supplying a toluene containing feedstock having a toluene purity greater than 90 wt. % to said reaction zone;
   (c) supplying hydrogen to said reaction zone;
   (d) operating said reaction zone under reaction severity conditions of space velocity temperature and pressure effective to cause the disproportionation of said toluene to benzene and xylene;
   (e) recovering a product stream from said reaction zone containing toluene, benzene and xylene;
   (f) thereafter supplying a toluene containing feedstock having a toluene content within the range of 80–90 wt. % toluene and a $C_6$–$C_8$ nonaromatic content within the range of 10–20% to said reaction zone;
   (g) operating said reaction zone under reaction severity conditions of space velocity, temperature and pressure which are more severe than the reaction severity conditions of subparagraph (d), and which are effective to cause the disproportionation of said toluene to benzene and xylene with concomitant cracking of said nonaromatic hydrocarbons to convert the predominant portion of said nonaromatic hydrocarbon content to lower molecular weight hydrocarbons to produce a lower boiling fraction in the LPG boiling range; and
   (h) recovering a product stream from said reaction zone containing toluene, benzene and xylene, together with $C_2$–$C_4$ hydrocarbons.

15. The process of claim 14 wherein said reaction zone is operated in subparagraph (g) at a lower space velocity than the space velocity in the reaction zone in subparagraph (d).

16. The process of claim 14 wherein said reaction zone is operated in subparagraph (g) at a pressure which is greater than the pressure of said reaction zone in the operation of subparagraph (d).

17. The process of claim 14 wherein said catalyst is promoted with a metal effective to enhance the hydrogenation activity of the catalyst.

18. The method of claim 17 wherein said mordenite disproportionation catalyst is promoted with nickel.

19. The method of claim 18 wherein said mordenite disproportionation catalyst is promoted with platinum or palladium.

* * * * *